US00PP09669P

United States Patent [19]

Van Rijn

[11] Patent Number: Plant 9,669

[45] Date of Patent: Oct. 22, 1996

[54] ANTHURIUM PLANT NAMED 'NATHALIE'

[75] Inventor: Magdalena J. M. Van Rijn, Schipluiden, Netherlands

[73] Assignee: Van Rijn Plants, Am Schipluiden, Netherlands

[21] Appl. No.: 510,415

[22] Filed: Aug. 2, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

The Anthurium plant 'Nathalie' is small with oval leaves. The spathe is pink with small oval lobes and is held by a peduncle above the leaves. The spadix is purple-red and this color is darkest at the distal end. 'Nathalie' grows quickly and has a compact growth habit.

3 Drawing Sheets

INTRODUCTION

The present invention comprises a new and distinct cultivar of Anthurium, botanically known as *Anthurium andreanum,* and referred to by the cultivar name 'Nathalie.'

The new cultivar is a product of a planned breeding program, and was originated from a cross made during such a program in Schipluiden, The Netherlands, on Mar. 28, 1990. The female or seed parent was the variety 'Southern Blush' and the male, or pollen parent, was the variety 'Jolanda.'

'Nathalie' was discovered and selected on Oct. 10, 1991 as a flowering plant within the progeny of the stated cross by Magdalena J. M. van Rijn in a controlled environment in Schipluiden. Subsequent asexual reproduction by tissue culture at the above location has demonstrated that the combination of characteristics as herein disclosed for the new cultivar are firmly fixed and are retained through successive generations of asexual reproduction.

The following traits have been repeatedly observed and in combination distinguish 'Nathalie' as a new and distinct cultivar.

1. Quick growth and quick flowering with easy induction of new flowering.

2. Strong root structure with a compact plant habit and good branching.

3. Small plants with dark green leaves and a small spathe.

4. Leaves are middle-sized with acute tips and are on short petioles. The petioles are green and contain anthocyanin.

5. Peduncles are short and green at their base with a reddish-brown color at the distal end. The peduncle in cross-section is elliptic.

6. The spathe is small with lobes that are free and broadly ovate in shape. The distal part of spathe is rounded and the tip is acuminate.

7. The main color of the spathe on the upper side is R.H.S. 52 C-D (HCC 621/1-621) with bright pink stains. The color of the lower side of the spathe is R.H.S. 155 D with pink stains that are HCC 621/2.

8. The short spadix narrows at the distal end. The longitudinal axis of the spadix is straight.

9. The color of the spadix is purple-red and the color is darkest at the distal end.

The following observations, measurements and values describe plants grown in Schipluiden, The Netherlands, under greenhouse conditions which closely approximate those generally used in horticultural practice. Color references are made to The Royal Horticultural Society Colour Chart (R.H.S.), and the Wilson Colour Chart except where general color terms of ordinary significance are used. The phenotype may vary significantly when grown under different conditions of temperature, light and other determining factors, without a change in genotype of the plant.

The color values were determined between 14:00 h and 14:30 h under natural light at 's-Gravenzande, The Netherlands. Light intensity was 1210 J/m$^2$.

DESCRIPTION OF THE PHOTOGRAPHIC DRAWINGS

Sheet 1 is a side perspective of 'Nathalie' grown in a 17 cm wide pot.

Sheet 2 is a closeup of the spathe and spandix.

Sheet 3 is a closeup of the spadix.

DETAILED DESCRIPTION

Classification:

*Botanical.*—*Anthurium andreanum,* cv 'Nathalie.'

*Commercial.*—'Nathalie'.

Parentage:

*Male parent.*—'Jolanda'.

Female parent.—'Southern Blush'.

Propagation: Tissue culture.

*Growth habit.*—Compact.

Plant: From 35 to 45 cm tall (with flowers 55–65 cm) and approximately 50 cm in diameter when fully grown.

Leaves:

*Form.*—ovate, acute tip, position of the lobes is free.

*Size.*—about 19 cm long ×15 cm wide

*Texture.*—weak blistering

*Veins.*—at base reddish-brown in color which turns brighter green than the color of the leaves towards the tip of the leaves.

*Color.*—Upper surface R.H.S. 137 C, lower surface R.H.S. 143 C.

*Buds.*—the closed bud has a pink color that is brighter than the opened flower; the veins are darker pink then the rest of the closed bud; the tip of the bud is green.

Spathe:

*Size.*—Approximately 7 cm long ×8 cm wide

*Color.*—Upper: Approximately ca. HCC 621/1-621 or R.H.S. 52 C-D Lower: Approximately ca. R.H.S. 155 D with pink stains of HCC 621/2, weak glossiness. Arrangement: Spathe is above leaves and the lobes of the spathe are free. Shape: broad ovate, distal part is rounded, the tip is acuminate. Flowering time: in Winter 6 weeks and in summer 3 months.

Reproductive organs:

*Spadix.*—Length 5.5 to 6.5 mm.; diameter 6–7 mm; in cross-section it is round, with a longitudinal axis that is straight and narrows at the distal end; the main color is purple-red becoming darker towards the distal end.

*Stamens.*—Protogynous purple-red color

*Anthers and filaments.*—No filaments, anthers sit directly on the spadix.

*Pollen.*—Color white cream.

Roots: roots are white yellow color of normal size.

Disease resistance: Unknown.

General observations: 'Nathalie' is a small plant with oval leaves. The spathe is also small with oval lobes and is held above the leaves. The spadix color is purple-red and is darkest in color at the distal end. 'Nathalie' is fast growing with a compact growth habit.

| | Comparative Varieties | |
|---|---|---|
| Characteristics | Cultivar 'Lady Jane' | Cultivar 'Nathalie' |
| Leaf Form | Small Ovate | Broad Ovate |
| Spathe Color | RHS 53 C-RHS 52A more to red | RHS 52C-D more to pink |
| Spadix color | bright pink | purple red |

I claim:

1. A new and distinct Anthurium plant named 'Nathalie', as herein described and illustrated.

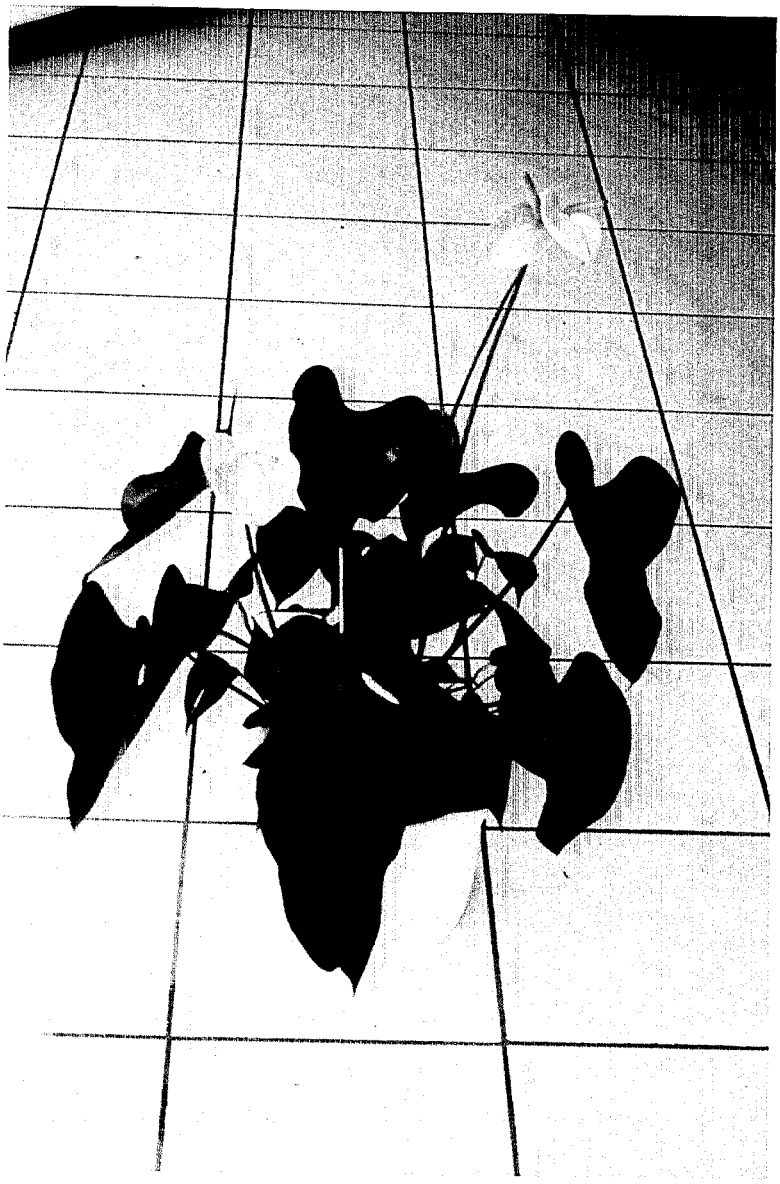

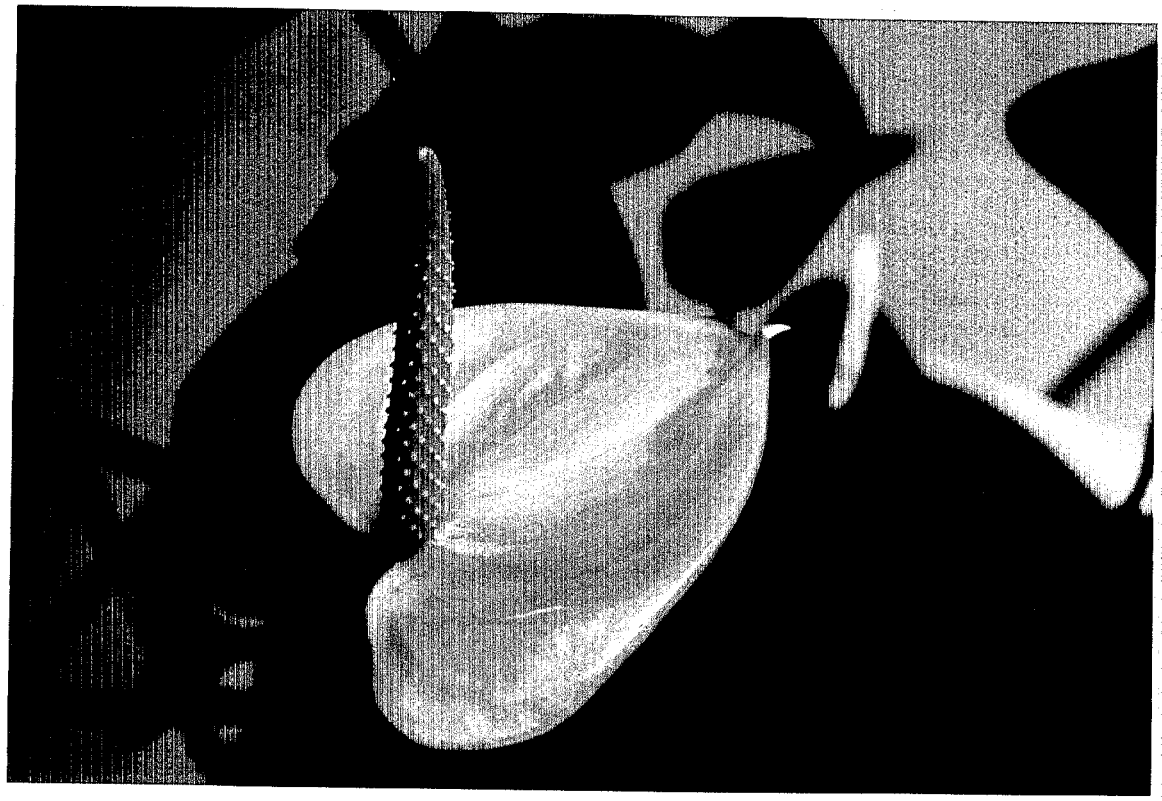

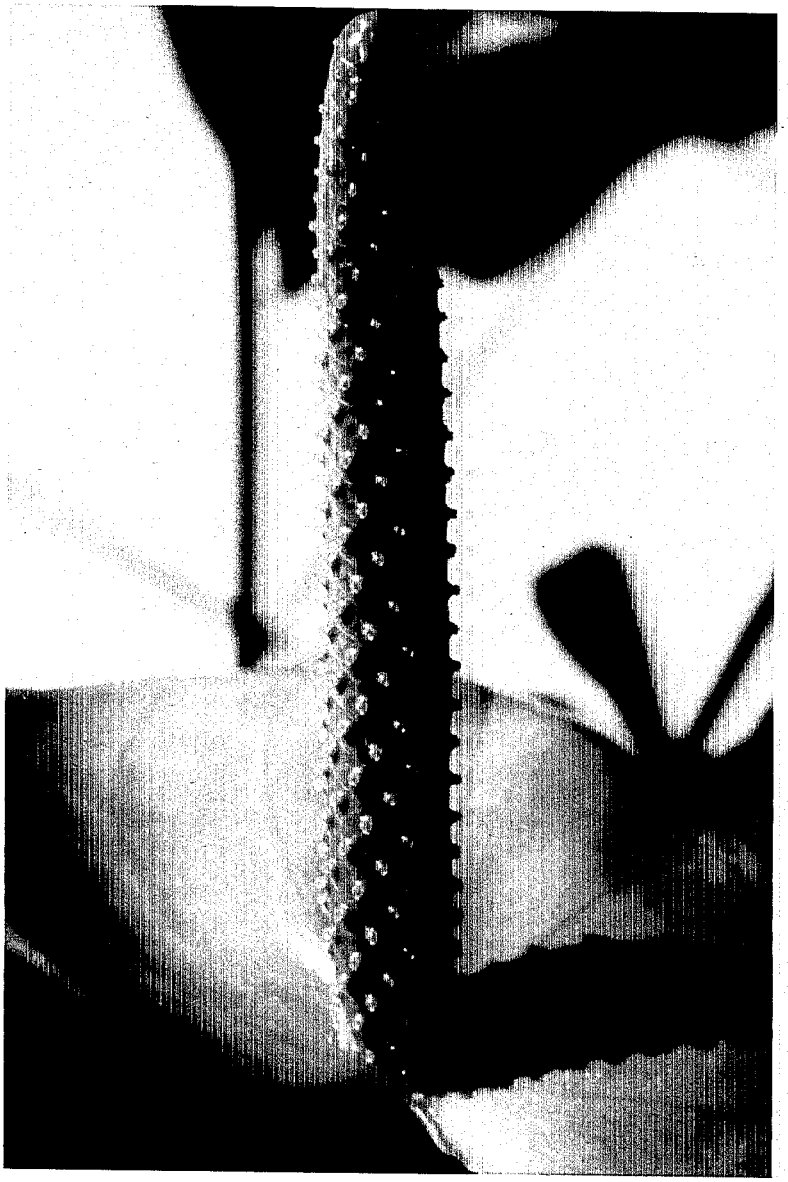

* * * * *